(12) United States Patent
Muller et al.

(10) Patent No.: US 6,928,139 B2
(45) Date of Patent: Aug. 9, 2005

(54) METHOD AND DEVICE FOR SAMPLING TISSUE DURING A RADIOLOGICAL EXAMINATION

(75) Inventors: Serge Muller, Guyancourt (FR); Andreas Rick, Schwerte (DE)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 10/125,312

(22) Filed: Apr. 17, 2002

(65) Prior Publication Data

US 2002/0159565 A1 Oct. 31, 2002

(30) Foreign Application Priority Data

Apr. 30, 2001 (FR) .............................................. 0105819

(51) Int. Cl.[7] .................................................. A61B 6/04
(52) U.S. Cl. ......................................................... 378/37
(58) Field of Search ........................................... 378/37

(56) References Cited

U.S. PATENT DOCUMENTS

| | | | | |
|---|---|---|---|---|
| 5,056,523 A | * | 10/1991 | Hotchkiss et al. | 600/427 |
| 5,081,357 A | * | 1/1992 | Agano | 250/589 |
| 5,240,011 A | * | 8/1993 | Assa | 600/564 |
| 5,568,533 A | * | 10/1996 | Kumazaki et al. | 378/156 |
| 5,964,715 A | * | 10/1999 | Thunberg | 600/562 |

\* cited by examiner

*Primary Examiner*—Craig E. Church
(74) *Attorney, Agent, or Firm*—Cantor Colburn LLP

(57) ABSTRACT

A method and device for sampling a fragment of tissue in which a contrast medium is injected into an organ to be examined and highlights parts containing that contrast medium in an image obtained by emitting a beam of X-rays. At least one pair of radiographic images is captured from a first position and a second position of an X-ray emitter during a phase of increasing attenuation due to the contrast medium. A specific area is identified from the pair of images in which a tissue fragment is to be sampled. The images of the pair of images are combined to determine the three-dimensional coordinates of the specific area.

21 Claims, 4 Drawing Sheets

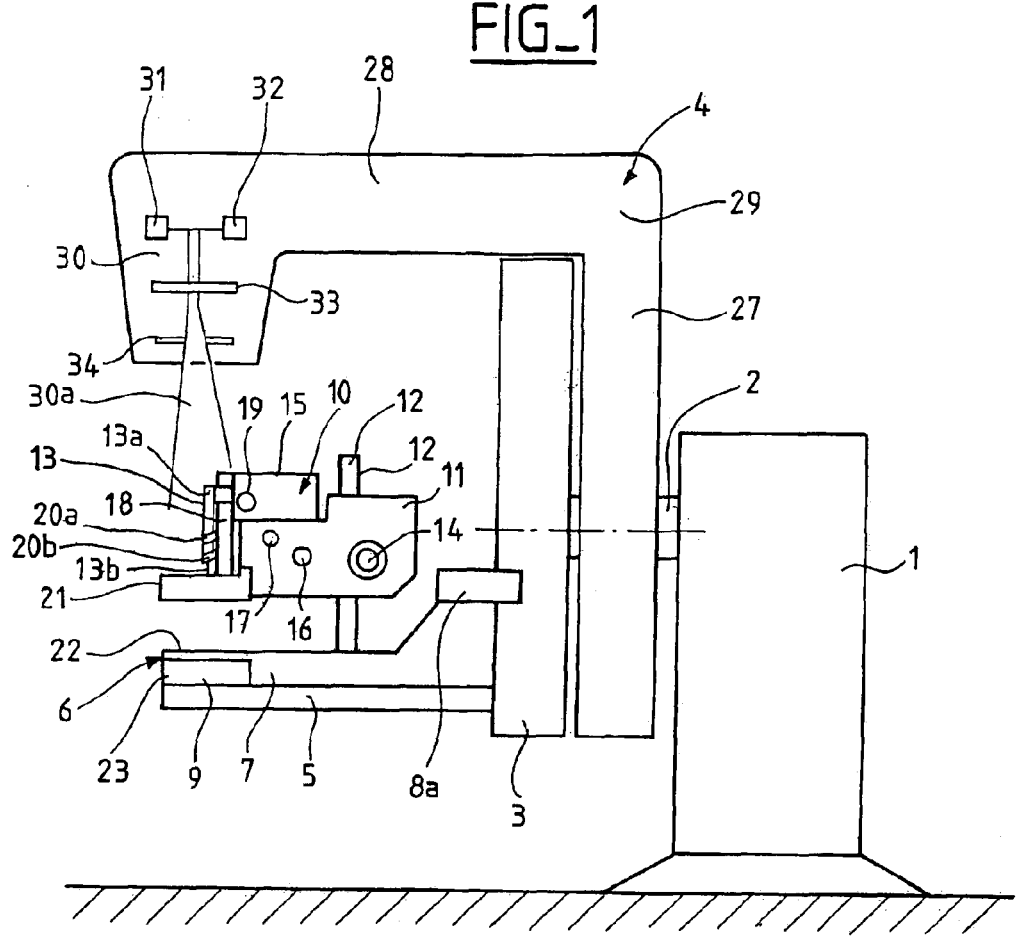
FIG_1
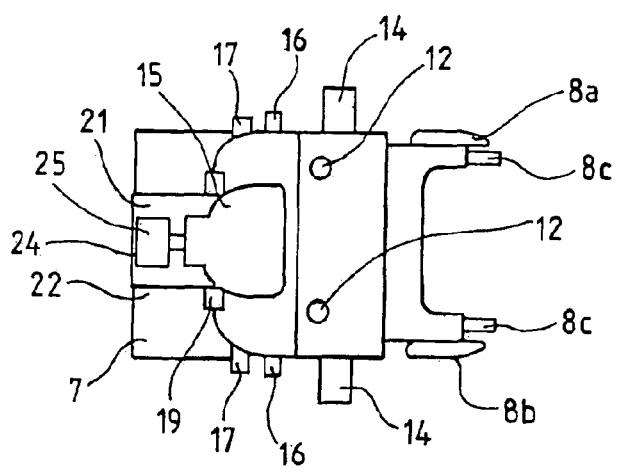
FIG_2

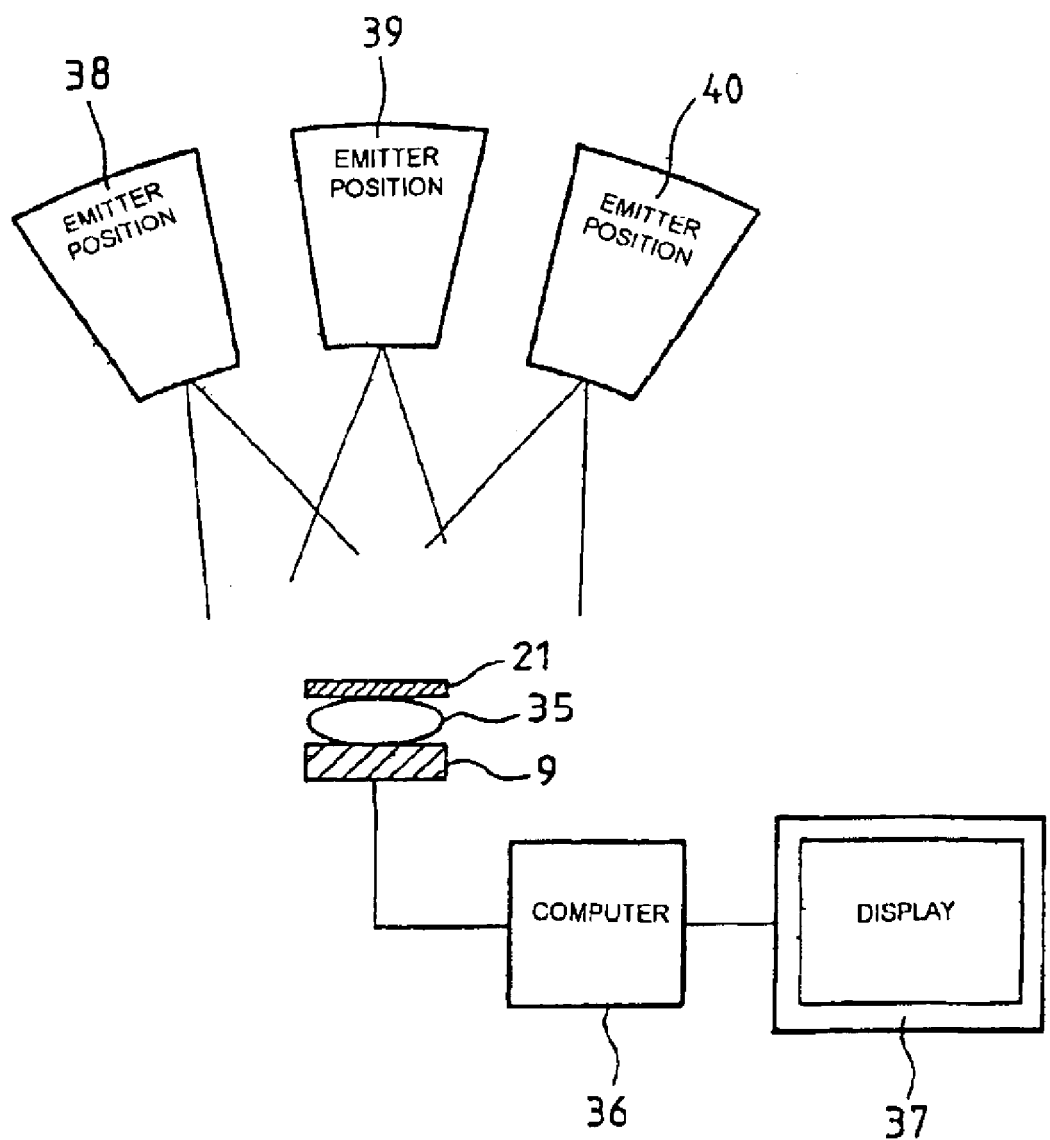

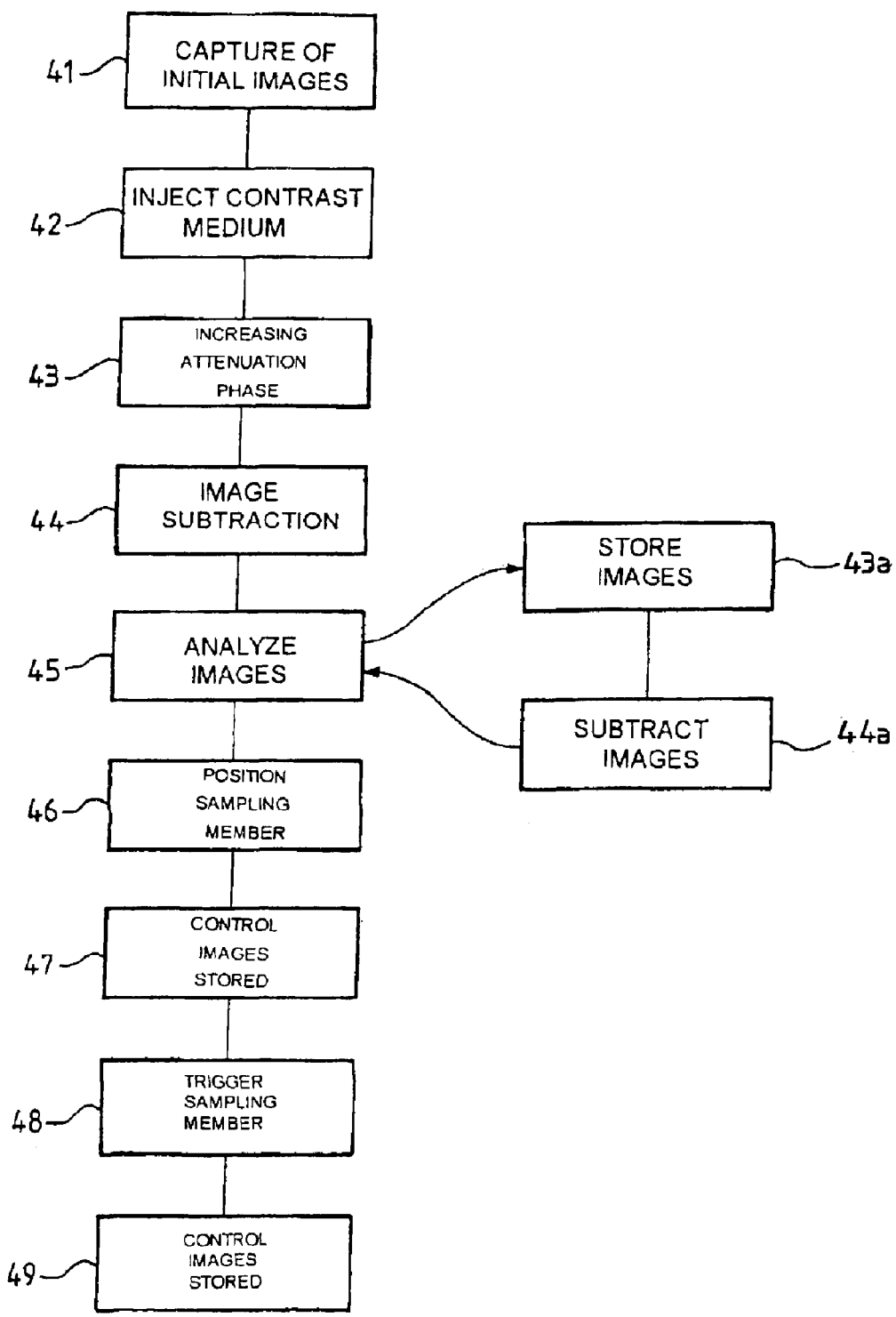

FIG_5
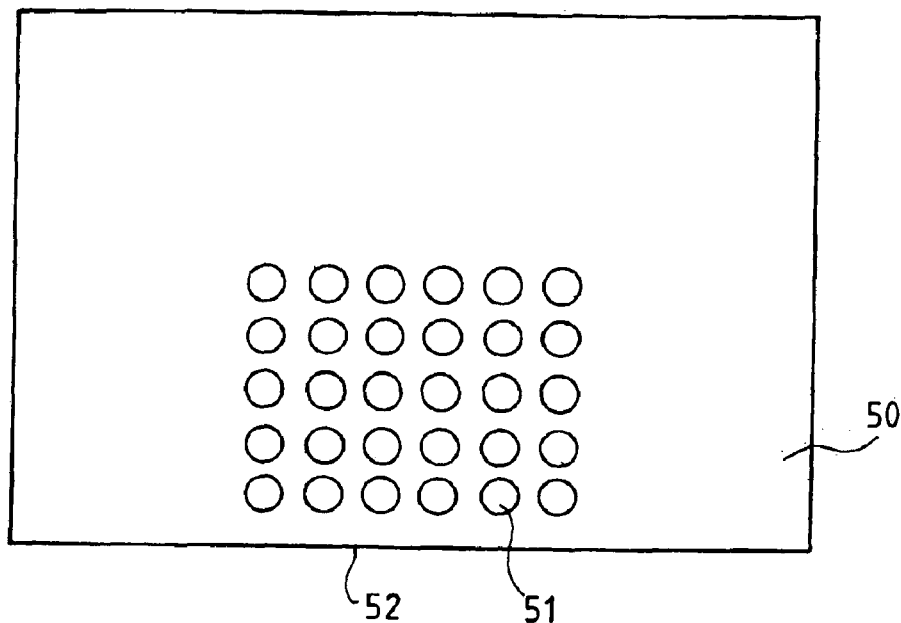
FIG_6
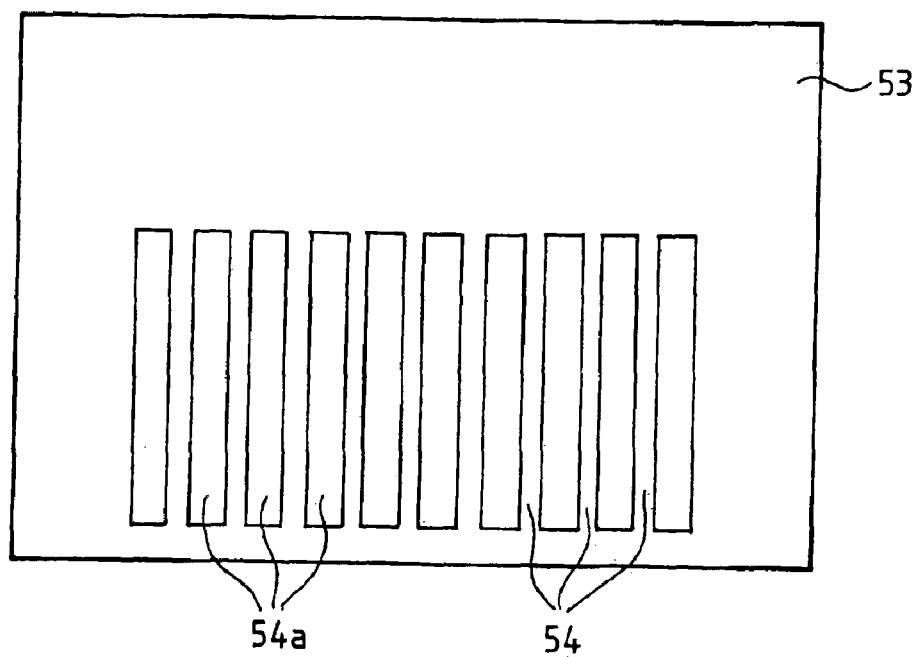

METHOD AND DEVICE FOR SAMPLING TISSUE DURING A RADIOLOGICAL EXAMINATION

CROSS-REFERENCE TO RELATED APPLICATIONS

This application claims the benefit of a priority under 35 USC 119 to French Patent Application No. 0105819 filed Apr. 30, 2001, the entire contents of which are hereby incorporated by references.

BACKGROUND OF THE INVENTION

The present invention relates to medical imaging and tissue sampling (biopsy), more particularly sampling mammary tissue.

A radiographic device, used for mammography, for example, includes an X-ray tube for forming and a collimator for delimiting a beam of X-rays, a radiological image receiver, and a positioner carrying the combination of the X-ray tube and the image receiver, the combination being movable about one or more axes. A radiographic apparatus for mammographic use is disclosed in EP-A-972 490.

Conventionally, to detect breast cancer, radiographic images are obtained and analyzed to deduce the probability of the presence of a malignant lesion in particular areas. If a suspect area is detected, a practitioner performs one or more biopsies to obtain tissue for histological analysis. If the lesion is visible on a radiographic image, the radiographic image guides a sampling member which performs the biopsy.

A disadvantage of using a radiographic image to guide a biopsy is that conventional radiographic images can detect only lesions accompanied by microcalcification or opacity of sufficient magnitude to be detected in a radiographic image. However, there are lesions that do not form microcalcification or opacity of sufficient magnitude to be detected and made the subject of a biopsy.

Furthermore, the presence of microcalcification in highly localized areas within the lesion does not enable the size and the shape of the lesion to be determined, for example, to consider surgical intervention. Microcalcification cannot indicate with a high level of confidence whether the lesion is malignant or not.

BRIEF DESCRIPTION OF THE INVENTION

An embodiment of the invention is a method for imaging lesions that can be used to guide a biopsy by means of images produced by the method.

An embodiment of the invention is a method of imaging lesions from which the extent and the shape of a lesion can be determined.

An embodiment of the invention is a method of imaging lesions that indicates whether or not a lesion is malignant.

An embodiment of the method is directed to sampling a fragment of tissue comprising the following steps. Injection of a contrast medium into the proximate area of an organ to be examined to highlight parts containing the contrast medium in an image obtained by emitting a beam of radiation for example, X-rays. Capturing at least one pair of radiographic images from a first position and a second position of the emitter of radiation during a phase of increasing attenuation due to the contrast medium. Identifying a specific area from the pair of images in which a tissue fragment is to be sampled. Combining the images of the pair of images to determine the three-dimensional coordinates of a suspect area.

An embodiment of the invention is a device for sampling a fragment of tissue, which device is disposed on a radiographic apparatus including means for emitting a beam of radiation for example, X-rays, and adapted to emit in the direction of an organ under study from at least two different positions; means for receiving the beam of radiation after it has passed through the organ under study and adapted to provide images of the beam of radiation; a fixed surface on the same side of the organ as the means for receiving; and a bearing plane on the opposite side of the organ to the means for receiving; and a means for sampling comprises a member disposed on a positioning device movable in three different directions on the side of the organ opposite the means for receiving.

BRIEF DESCRIPTION OF THE DRAWINGS

The present invention will be better understood from the detailed description of embodiments, which description is given by way of non-limiting example and with reference to the accompanying drawings, in which:

FIG. 1 is a schematic elevation view of an apparatus which includes a device according to an embodiment of the invention for sampling fragments of mammary tissue;

FIG. 2 is a plan view of a tissue fragment sampling device;

FIG. 3 is a schematic side view of the apparatus with the radiation emitter in several radiographic imaging positions.

FIG. 4 is an embodiment of the method;

FIG. 5 is a plan view of one embodiment of a bearing plane; and

FIG. 6 is a plan view of another embodiment of a bearing plane.

DETAILED DESCRIPTION OF THE INVENTION

FIGS. 1 and 2 shows an apparatus for mammography including a base 1 resting on a floor and supporting by means of a horizontal shaft 2, a fixed vertical support column 3 at the end of the shaft 2 opposite the base 1, and an assembly 4 that can rotate about the shaft 2.

A plate 5 extends horizontally from the side of the column 3 opposite the base 1 and supports a movable assembly 6 which includes a plane support member 7 extending in a horizontal plane and resting on the plate 5. The support member 7 includes fixing lugs 8a, 8b adapted to hold the support member 7 horizontal and in contact with the support column 3. Horizontal shafts 8c near the fixing lugs 8a, 8b are adapted to cooperate with holes in the support column 3 to define the position of the assembly 6 in the horizontal plane. A horizontally disposed receiver 9 is disposed in the plane of the support member 7 and at the end of the support member 7 opposite the support column 3.

A displacement device 10 on the support 7 includes a first member 11 which can move vertically on two parallel rods 12 projecting vertically from the support member 7 and provided with a positioning thumbwheel 14. A second member 15 disposed on the first member 11 so that it can move along two perpendicular horizontal axes and is provided with a positioning thumbwheel 16 for the first horizontal axis and a positioning thumbwheel 17 for the second horizontal axis. A vertical retaining finger 18 mobile vertically on the member 15 is provided with two fixing lugs 20a, 20b extending in two horizontal planes on the side opposite the base 1 and in an area vertically above the receiver 9. A thumbwheel 19 controls the position of the retaining finger 18 manually.

The fixing lugs 20a, 20b are for fixing a sampling member 13 having a vertical mobile part 13a provided at its lower end with a needle 13b that is oriented vertically downwards and is adapted to sample a fragment of tissue when it is pressed into a layer of tissue. The moving part 13a enables the needle 13b to be inserted rapidly and to a predetermined depth into the organ under study so that the needle 13b can sample tissue in the selected area. Fast insertion of the needle 13b prevents the tissue moving when the needle is inserted, and sampling is therefore effected in the required area.

A bearing plane 21 is fixed to the member 11 and extends horizontally from the member 11 in an area vertically facing a fixed surface 22 above the receiver 9 and in a plane between the sampling member 13 and the receiver 9. The end 24 of the bearing plane 21 opposite the member 11 is at substantially the same vertical level as an end 23 of the support member 7 horizontally opposite the base 1.

FIG. 2 shows that the bearing plane 21 has a rectangular hole 25 through it in the vicinity of the end 23. The hole 25 has one side parallel to the ends 24. The dimensions of the hole 25 are greater than those of the sampling member 13 to provide the sampling member 13 with access to a substantial area of the breast under study.

The member 15 is shown horizontally in an extreme position in which the fixing lugs 20a, 20b are vertically outside the area of the hole 25 and in the vicinity of the member 11. The member 15 is adapted to be moved from this position toward the end 24.

The generally L-shaped assembly 4 includes a first segment 27 freely rotatable on the shaft 2 and disposed axially on the shaft 2 between the support column 3 and the base 1. A second segment 28 extends perpendicularly from one end 29 of the first segment 27 so that the segment 27 can pivot about the shaft 2 without the support column 3 impeding rotation of the segment 28. At the end opposite the end 29 the segment 28 supports an X-ray emitter 30 having an anode 31, a cathode 32 enclosed in a vacuum in a sealed enclosure, producing a beam of X-rays 30a oriented toward the receiver 9, a filter 33 and a collimator 34 disposed between the anode-cathode assembly 31, 32 and the receiver 9.

In operation, the emitter 30 produces a beam of X-rays 30a that passes through the filter 33, the collimator 34, the bearing plane 21 and finally the organ under study, before reaching the receiver 9. The receiver 9 emits an image representative of the photons received and which therefore depends on the characteristics of the beam emitted by the emitter 30, the filter 33, the organ under study and the emitter itself.

FIG. 3 shows three different positions 38, 39, 40 of the emitter 30, which correspond to three different rotation angles of the segment 27 relative to the shaft 2, and which enable a beam of X-rays to be emitted toward the organ under study. An organ 35 under study is shown diagrammatically between the bearing plane 21 and the receiver 9, which sends data to a computer 36 which can be connected to a display screen 37 on which radiographic images appear.

The computer 36 includes a microprocessor, a memory, and a computation and/or control program stored in memory and adapted to be executed by the microprocessor.

To study a breast, a patient is seated at the end 24 of the assembly 6 so that a breast can be placed between the fixed surface 22 and the bearing plane 21, preferably centered in the hole 25. The thumbwheel 14 is used to lower the positioning device 10 vertically, carrying along the bearing plane 21, to compress the breast between the bearing plane 21 and the fixed surface 22. To guarantee accurate sampling, the pressure must be sufficient for the breast not to move during the capture of radiographic images and the sampling of a fragment of mammary tissue. On the other hand, because a contrast medium is used, the pressure applied must not impede the circulation of blood in the breast. Nevertheless, areas exhibiting high vascularization due to a lesion are larger than the microcalcification that generally accompanies lesions, which provides a wider area for sampling tissue and ensures sampling of a fragment of tissue whose histological analysis will be pertinent.

Before taking the sample, the sampling member 13 is positioned manually by means of the thumbwheels 16, 17, 19 or by an automatic device, not shown in the drawing. The positioning device 10 includes position sensors adapted to transmit the coordinates of the sampling member 13 to the computer 36. The sampling member 13 can be triggered manually or automatically to take the sample.

The contrast medium can be injected into the vessels of an organ to be examined, for example a breast. The contrast medium can be based on iodine. Generally, suspicious lesions sometimes present microcalcification. These lesions are easier to detect with a contrast medium because these lesions exhibit high or considerable vascularization. When a contrast medium diffuses into the organ, a large quantity of the contrast medium is therefore found in these lesions. Detecting lesions by detection of dense vascularization also indicates the size and the shape of the lesion, unlike detection of microcalcification. These characteristics can then assist a future surgical procedure, which comprises removing the lesion from the organ concerned. Hence, the advantage of knowing the size and the shape of the lesion, for example, to decide the best site for an incision.

A pair of initial images is preferably captured from the first and second positions of the emitter before injecting the contrast medium.

In one embodiment of the invention at least one second pair of images is taken from the first and second positions of the emitter after injecting the contrast medium.

To obtain images with enhanced contrast, at least one second pair of images is preferably captured at the end of a phase of increasing attenuation due to the contrast medium.

In one embodiment at least one image is captured from the first or second position of the emitter during a phase of increasing attenuation due to the contrast medium after injecting the contrast medium and before capturing the first pair of images. It is then possible to detect the end of a phase of increasing attenuation due to the contrast medium, in order to capture a pair of images during the end of this phase of attenuation due to the contrast medium.

Each image of the pair of initial images may be subtracted from each image of the pair of images or each pair of images obtained after injecting the contrast medium. Image processing produces pairs of images on which feature only changes in the attenuation due to the contrast medium that occurred during the diffusion of the contrast medium between the injection of the contrast medium and the capture of a given pair of images.

In one embodiment the sampling member is positioned manually.

In one embodiment the sampling member is positioned automatically.

The sampling member is preferably triggered manually.

An a priori control image may be captured from the first and/or the second position of the emitter when the sampling member has been positioned to sample a fragment of tissue. This image is used to control the position of the sampling member relative to the specific area.

An a posteriori control image may be captured from the first and/or the second position of the emitter when the sampling member is in the sampling position.

The device preferably includes means for injecting a contrast medium which highlights parts containing the contrast medium on a stored image produced by emitting a beam of radiation.

In one embodiment the bearing plane has at least one passage through it which is larger than the means for sampling.

In one embodiment the bearing plane has a plurality of passages through it which are larger than the sampling member.

In one embodiment the bearing plane includes regularly spaced parallel plates fixed at their ends to leave passages between two adjacent plates. The plates are may be made of a flexible material. Two adjacent plates can be separated enough for the sampling member to pass between them.

The positioning device is adapted to orient the sampling member angularly about at least one axis of rotation.

An embodiment of the method is shown in FIG. 4.

In step 41, an initial pair of images is captured from positions 38, 40 of the emitter, before injecting a contrast medium. Conventional mammographic images are obtained in which lesions of the glandular tissue are difficult to distinguish from healthy parts of the glandular tissue and adipose tissue.

In step 42, the contrast medium is injected manually or by means of an injection system, which can be controlled by the computer 36. The contrast medium attenuates the beam of X-rays 30a traveling toward the receiver 9. After it is injected, the contrast medium diffuses into the blood network. Because lesions exhibit high vascularization, a large quantity of the contrast medium is found in the area of lesions, which enables them to be detected on an image obtained after injecting the contrast medium.

In step 43, a first pair of images is captured from positions 38, 40 of the emitter 30, after injecting the contrast medium and during a phase of increasing attenuation due to the medium. The duration of the phase of increasing attenuation due to the contrast medium can be estimated as a function of parameters such as the thickness of the breast or its radiographic density. It can also be estimated by means of a preliminary examination enabling diffusion of the contrast medium in the breast to be viewed.

In step 44, a subtraction operation is effected to eliminate the images initially obtained from positions 38, 40 of the emitter 30 from the images obtained in step 43 from the same respective positions 38, 40 of the emitter 30. The images taken in step 43 have a high contrast due to the diffusion and therefore the presence of the contrast medium in the breast. Subtracting these images eliminates from the images captured in step 43 structures with relatively little vascularization, which are therefore relatively little charged with contrast medium, whose gray level varies little between the images captured in step 41 and the images captured in step 43.

In step 45, the images obtained after step 44 are analyzed to determine, where applicable, one or more suspect areas from which tissue is to be sampled.

If the attenuation due to the contrast medium is considered to be still increasing, a step 43a can be executed to store a second pair of images from positions 38 and 40 of the emitter 30 during the end of the phase of increasing attenuation due to the contrast medium. A step 44a then subtracts each initial image obtained from positions 38, 40 of the emitter 30 from each image obtained in step 43a from the same respective positions 38, 40 of the emitter 30. By subtracting these initial images, images are obtained featuring only the differences of attenuation between the images concerned. Here images are obtained in which it is possible to see the difference in attenuation due to the presence of the contrast product. This is then followed by a step 45.

In step 45, a suspect area on a pair of images is identified, for example, on the display screen 37. This identification indicates the two-dimensional coordinates of the suspect area in each image of the pair. Knowing the three-dimensional coordinates of the positions 38, 40 and of the position of the receiver 9, it is possible to determine by simple geometrical analysis the three-dimensional coordinates of the suspect area from the two-dimensional coordinates of the suspect area in each image of the pair images.

In step 46, by means of the positioning device, the sampling member 13 is disposed vertically over the suspect area, near the outside surface of the organ under study.

In step 47, a pair of control images is stored for apriori control of the position of the sampling member 13 before a tissue fragment is actually sampled. If its position is not correct, positioning of the sampling member 13 can be started over. The control images can be taken during a phase in which the attenuation due to the contrast product is still significant. The position of the sampling member 13 can instead be verified by superposing a pair of control images, in which the product may not be very visible, but in which the sampling member 13 can be seen clearly, and a pair of images taken during step 44 or 46.

In step 48, the sampling member 13 is triggered and penetrates vertically into the breast as far as the suspect area, in the precise position determined in step 45. A positioning device can be used instead whose member 15 orients the sampling member 13 so that the needle 13b enters along an inclined axis.

In step 49, a pair of control images is stored for a posteriori control of the position of the sampling member 13 relative to the suspect area. It is thus possible to determine if a tissue fragment has been sampled from the suspect area. If not, sampling can be started over. The control images can be captured in a phase in which the attenuation due to the contrast medium is still significant. The position of the sampling member 13 can instead be verified by superposing a pair of control images, in which the product may not be very visible, but in which the sampling member 13 can be seen clearly, and a pair of images taken during step 44 or 46.

A plurality of pairs of images can instead be captured during the phase of increasing attenuation due to the contrast medium, in order to determine how the contrast medium is diffusing in the breast and to estimate the end of the period of the phase of increasing attenuation due to the contrast medium.

In a second embodiment, during the phase of increasing attenuation due to the contrast medium, a plurality of images can be captured from a single position of the emitter 30 to determine how the contrast medium is diffusing into the breast and to estimate the end of the period of the phase of increasing attenuation due to the contrast medium. It is not necessary to take images from two different positions during this phase, because no sampling is done.

If more than one suspect area is detected, the areas detected can have different contrast medium diffusion dynamics. Storing the images means that tissue can be sampled subsequently. Superposing images enables the position of the sampling member 13 to be verified if the contrast product is no longer visible. Furthermore, the dynamics of diffusion of the contrast medium in a lesion provides information on the nature of the lesion. The faster the contrast product is absorbed and eliminated, the more suspect the lesion.

In FIG. 5, a rectangular bearing plate 50 has a plurality of circular holes 51 through it forming a rectangular area near one end 52 of the bearing plane which bears on a substantial part of the breast. In this embodiment the positioning device 10 advantageously enables the sampling member 13 to be oriented about a rotation axis so that it can reach all parts of the breast under study. Each hole 51 is larger than the sampling member 13 so that the sampling member 13 can pass through it.

In FIG. 6, a bearing plane 53 comprises a plurality of regularly spaced, parallel and identical plates 54 retained at their ends and with passages 54a through them, forming a rectangular area bearing on a substantial part of a breast. The plates 54 are made from a material that is sufficiently flexible to enable them to deform in the horizontal plane. It is therefore possible to increase the size of the corresponding passage 54a for the sampling member 13 to pass through by spreading apart two adjacent plates 54.

One skilled in the art can choose the material of the anode of the X-ray emitter, the composition of the filter, the supply voltage and the contrast medium in a coordinated way to obtain a high image quality.

The linear attenuation coefficient of iodine, which can be used as a contrast medium, as a function of the emitted energy of the X-rays, has a local maximum at around 33 keV. The coefficient of linear attenuation of adipose tissue as a function of the energy of the X-rays is extremely low for values of the order of 30 to 40 keV and higher for lower energies, for example.

In other words, an energy of the order of 33 to 45 keV obtains the benefits of low attenuation due to adipose tissue, which forms noise in the image, and a relatively high attenuation due to the contrast medium. The ratio of the attenuation by iodine to the attenuation by adipose tissue is usually greater than 200 in the range from 33 to 45 keV.

The spectrum of a beam of X-rays emitted by mammography apparatus having a molybdenum anode, a molybdenum filter and a supply voltage of the order of 25 kV has an area of high energy density for energy values from 15 to 20 keV.

The spectrum of a beam of X-rays emitted by mammography apparatus having a molybdenum anode, a copper filter and a supply voltage of the order of 45 kV has an area of high energy density for energy values from 30 to 45 keV.

It is therefore preferable to use a supply voltage of the order of 45 kV and a copper filter, which produces a flux of photons having a high energy density in the range from 30 to 45 keV, which is close to the maximum local absorption of iodine, which occurs at 33 keV.

More generally, a copper filter from 0.2 to 0.5 mm thick, and preferably from 0.3 to 0.4 mm thick, can be used. The supply voltage can be from 40 to 50 kV, preferably from 45 to 49 kV. A filter containing zinc could also be used.

The sampling method can detect a suspect area in an organ under study and at the same time take a tissue sample for histological examination. The method produces images of high quality showing only highly vascularized areas that are potentially lesions, those images being used to position a sampling member 13. The method can also determine accurately the size of the lesion in question, for example for the purposes of a surgical procedure. Samples can be taken throughout the specific area, guaranteeing the results of histological investigation of the tissue fragment.

Various modifications in structure and/or steps and/or function may be made by one skilled in the art without departing form the scope and extent of the invention as recited in the claims.

What is claimed is:

1. A method of sampling a fragment of tissue, comprising:
    obtaining an initial pair of radiographic images of an organ to be examined from a first position and a second position by a radiation emitter before injecting a contrast medium;
    injecting a contrast medium into the organ to be examined;
    obtaining at least one pair of radiographic images from the first position and the second position by the radiation emitter during a phase of increasing attenuation due to the contrast medium;
    obtaining at least one second pair of radiographic images from the first position and the second position by the radiation emitter at the end of the phase of increasing attenuation due to the contrast medium;
    in response to the at least one pair and the at least one second pair of radiographic images, identifying a specific area in which the fragment is to be sampled; and
    combining images of the initial pair of radiographic images, the at least one pair of radiographic images, the at least one second pair of radiographic images, or any combination comprising at least two of the foregoing pairs of images to determine the three-dimensional coordinates of the specific area.

2. The method according to claim 1 wherein an a posteriori control image is taken from the first and/or the second position of the emitter when a sampling member for the fragment is in the sampling position.

3. The method according to claim 1 wherein an a priori control image is taken from the first and/or the second position of the emitter when a sampling member for the fragment has been positioned to sample a fragment of tissue.

4. The method according to claim 1 wherein a sampling member for the fragment is manually initiated.

5. The method according to claim 1 wherein a sampling member for the fragment is positioned automatically.

6. The method according to claim 1 wherein a sampling member for the fragment is positioned manually.

7. The method according to claim 1 wherein at least one image is captured from the first or second position of the emitter during a phase of increasing attenuation due to the contrast medium after injecting the contrast medium and before obtaining a first pair of images.

8. The method according to claim 1 wherein the pair of initial images is subtracted from a pair of images or each pair of images obtained after injecting the contrast medium.

9. A device for sampling a fragment of tissue, which device is disposed on a radiographic apparatus, the apparatus comprising:
    means for emitting radiation in a direction of an organ under study from at least two different positions;
    means for receiving the radiation after it has passed through the organ under study to provide an image of the radiation;

wherein the means for emitting radiation includes an emission filter for highlighting a contrast medium in the radiographic image obtained by the means for receiving;

the device comprising:
  a support surface on the same side of the organ as the means for receiving;
  a bearing plate on the opposite side of the organ to the means for receiving, the bearing plate comprising a flexible material sufficient to allow the bearing plate to deform in a horizontal plane in response to the organ under study being compressed between the support surface and the bearing plate with sufficient pressure for the organ under study not to move during the sampling of the fragment of tissue while also not impeding the circulation of blood in the organ under study;
  means for injecting a contrast medium; and
  means for sampling the fragment disposed on means for positioning movable in three different directions on the side of the organ opposite the means for receiving;
  wherein the means for positioning movable in three different directions comprises means for manually positioning movable in three different directions and means for automatically positioning movable in three different directions.

10. The devise according claim 9 wherein the bearing plate has at least one passage that is larger than the means for sampling.

11. The device according to claim 10 wherein the bearing plate has a plurality of passages that is larger than the means for sampling.

12. The device according to claim 9 wherein the means for positioning movable in three different directions is adapted to orient the means for sampling angularly about at least one rotation axis.

13. The device according to claim 9 wherein:
  the support surface comprises a fixed surface; and
  the bearing plate comprises a planar surface.

14. A device for sampling a fragment of tissue, which device is disposed on a radiographic apparatus, the apparatus comprising:
  means for emitting radiation in a direction of an organ under study from at least two different positions;
  means for receiving the radiation after it has passed through the organ under study to provide an image of the radiation;
  the device comprising:
    a support surface on the same side of the organ as the means for receiving;
    a bearing plate on the opposite side of the organ to the means for receiving; and
    means for sampling the fragment disposed on means for positioning movable in three different directions on the side of the organ opposite the means for receiving;
    wherein the bearing plate includes a plurality of spaced plates fixed at their ends to provide passages between two adjacent plates.

15. The device according to claim 14 wherein the plates are made of flexible material to enable two adjacent plates to be separated enough for the means for sampling to pass between them.

16. The device according to claim 14 wherein the plurality of spaced plates comprises a plurality of regularly spaced parallel plates.

17. The device according to claim 14 wherein the means for emitting radiation includes an emission filter for highlighting a contrast medium in the radiographic image obtained by the means for receiving.

18. The device according to claim 17 wherein the plates are made of flexible material to enable two adjacent plates to be separated enough for the means for sampling to pass between them.

19. A device for sampling an object, which device is disposed on a radiographic apparatus, the apparatus including
  means for emitting radiation in a direction of an object under study from at least two different positions;
  means for receiving the radiation after it has passed through the object under study to provide an image of the radiation; the device comprising:
    a support surface on the same side of the object as the means for imaging;
    a bearing plate on an opposite side of the object to the means for imaging;
    means for positioning movable in multiple directions on the side of the object opposite the means for imaging, the means for positioning movable in multiple directions comprising means for manually positioning movable in multiple directions and means for automatically positioning movable in multiple directions; and
    means for sampling disposed on the means for positioning;
    wherein the bearing plate has a plurality of passages formed by a plurality of spaced plates, the plurality of passages sufficient to allow the passage of the means for sampling, and the plurality of spaced plates comprising a flexible material sufficient to allow them to deform in a horizontal plane in response to the object under study being compressed between the support surface and the bearing plate with sufficient pressure for the object under study not to move during the sampling.

20. The device according to claim 19 comprising:
  means for injecting a contrast medium into the object.

21. The device according to claim 19 wherein the means for positioning movable in multiple directions orients the means for sampling about at least one axis of rotation.

* * * * *

UNITED STATES PATENT AND TRADEMARK OFFICE
CERTIFICATE OF CORRECTION

PATENT NO. : 6,928,139 B2 Page 1 of 1
APPLICATION NO. : 10/125312
DATED : August 9, 2005
INVENTOR(S) : Serge Muller et al.

It is certified that error appears in the above-identified patent and that said Letters Patent is hereby corrected as shown below:

Title Page,
(56) References Cited, insert therefor
--6,022,325    2/2000   Siczek, et al................600/568
4,817,125      3/1989   Sklebitz, et al..............378/152
4,821,727      4/1989   Levene, et al...............128/653
4,943,986      7/1990   Barbarisi.....................378/37
4,723,261      2/1998   Janssen, et al...............378/99

EP    972,490  1/2000
WO  9,005,485  5/1990
EP    483,005  4/2002
EP    146,511  6/1985 --

Column 6,
Line 25, after "for" delete "apriori" and insert therefor --a priori--.

Signed and Sealed this

Fifth Day of September, 2006

JON W. DUDAS
*Director of the United States Patent and Trademark Office*